(12) United States Patent  
Ein-Gal (10) Patent No.: US 6,497,704 B2
(45) Date of Patent: Dec. 24, 2002

(54) ELECTROSURGICAL APPARATUS

(76) Inventor: Moshe Ein-Gal, 30 Azar Street, Ramat Hasharon 47203 (IL)

( * ) Notice: Subject to any disclaimer, the term of this patent is extended or adjusted under 35 U.S.C. 154(b) by 0 days.

(21) Appl. No.: 09/824,693

(22) Filed: Apr. 4, 2001

(65) Prior Publication Data

US 2002/0147446 A1 Oct. 10, 2002

(51) Int. Cl.$^7$ ................................................ A61B 18/18
(52) U.S. Cl. ........................................ 606/41; 607/101
(58) Field of Search .............................. 606/41, 42, 45, 606/46, 48, 50; 607/101, 102, 115, 116

(56) References Cited

U.S. PATENT DOCUMENTS

| | | | |
|---|---|---|---|
| 5,100,388 A | | 3/1992 | Behl et al. |
| 5,222,953 A | * | 6/1993 | Dowlatshahi ............... 600/549 |
| 5,304,214 A | | 4/1994 | DeFord et al. |
| 5,348,554 A | | 9/1994 | Imran et al. |
| 5,431,645 A | * | 7/1995 | Smith et al. ................ 600/106 |
| 5,431,649 A | * | 7/1995 | Mulier et al. ................ 600/374 |
| 5,472,441 A | * | 12/1995 | Edwards et al. ............ 128/898 |
| 5,507,743 A | * | 4/1996 | Edwards et al. ............ 600/373 |
| 6,004,269 A | * | 12/1999 | Crowley et al. ............ 600/374 |
| 6,010,476 A | | 1/2000 | Saadat |
| 6,016,809 A | | 1/2000 | Mulier et al. |
| 6,066,134 A | | 5/2000 | Eggers et al. |
| 6,102,046 A | | 8/2000 | Weinstein et al. |
| 6,112,123 A | | 8/2000 | Kelleher et al. |
| 6,132,426 A | | 10/2000 | Kroll |
| 6,280,441 B1 | * | 8/2001 | Ryan ........................... 600/373 |
| 6,286,512 B1 | * | 9/2001 | Loeb et al. .................. 128/898 |

* cited by examiner

Primary Examiner—Michael Peffley
(74) Attorney, Agent, or Firm—David Klein; Dekel Patent Ltd.

(57) ABSTRACT

Electrosurgical apparatus including a plurality of electrodes adapted to deliver radio frequency (RF) energy to a tissue and a manipulator in operable connection with the electrodes adapted to move the electrodes. In one embodiment, the electrodes comprise helical electrodes, which may be configured as a pair of bipolar concentric (sharing a common center) or eccentric (off-center) helices, for example.

3 Claims, 6 Drawing Sheets

ELECTROSURGICAL APPARATUS

FIELD OF THE INVENTION

The present invention relates to electrosurgical apparatus for tissue ablation generally, and particularly to electrosurgical apparatus for radio frequency (RF) tissue ablation.

BACKGROUND OF THE INVENTION

Radio frequency (RF) tissue ablation is a well-known technique for making thermal lesions in the vicinity of an uninsulated tip of an electrode due to tissue coagulation caused by resistive heating. The electrode can be applied directly on superficial structures, surgically, endoscopically, laparascopically, or even via a transcatheter access such as a treatment for symptomatic cardiac arrhythmias. If the electrode is formed as a needle, then the electrode may be inserted interstitially, and guided by imaging.

As is known in the art, resistive heating is proportional to the square of the current density, the latter being inversely proportional to the square of the distance from the ablation electrode. Therefore, resistive heating decreases from the ablation electrode with the distance to the fourth power. In other words, significant resistive heating only occurs within a narrow rim (of a few millimeters) of tissue in direct contact with the ablation electrode. Deeper tissue heating occurs as a result of passive heat conduction from that rim.

A general problem in RF tissue ablation is limitation in lesion size. Increasing the power to the electrode or exposure time to the tissue increases the amount of energy delivered around the electrode and thereby increases the lesion size. However, at high temperatures (e.g., above 100° C.) at the electrode-tissue interface, the impedance increases significantly because of desiccation followed by charring around the electrode tip. This leads to an abrupt fall in lesion current (and delivered effect) and no further energy is delivered around the electrode, and no further tissue heating occurs. This phenomenon tends to limit lesion size in the transverse direction around the electrode. The longitudinal dimension of the lesion is basically dependent on the length of the uninsulated part of the electrode.

Tissue adhesion and limited lesion size are just two examples of problems associated with RF tissue ablation. Another problem occurs when attempting to ablate tissue in difficult-to-reach locations, such as the lower esophagus. It is difficult to control the depth of the ablation into the tissue and to obtain a uniform ablation over the entire surface area that needs to be ablated. Surface irregularities, folds into the tissue, and variations in the anatomical configurations of body cavities increase the difficulty of achieving uniform RF tissue ablation. As a result, only a portion of the tissue to be ablated may be destroyed, and in some areas, more tissue may be ablated than was intended.

Attempts have been made in the prior art to overcome the abovementioned problems. One known solution is that of "electrolyte-assisted" ablation. This form of ablation relies on contacting the tissue to be ablated with an electrolyte, such as a fluid or gel. Electrical energy is applied through the electrolyte to the tissue in contact with the electrolyte. Because the electrical resistance of the electrolyte-tissue interface is significantly high relative to the resistance of the electrolyte itself, most of the energy will be dissipated at this interface in the form of heat, leading to thermal ablation of the superficial tissue at this interface. Introduction of a conducting and/or cooling liquid into the treated area generally increases the coagulated volume and tends to reduce tissue adhesion. Electrolyte-assisted ablation is also effective in difficult-to-reach locations, because the liquid or gel electrolyte effectively bathes the entire surface area of the tissue that is to be ablated.

One example of electrolyte-assisted ablation is discussed in U.S. Pat. No. 6,112,123 to Kelleher et al., assigned to Endonetics, Inc., San Diego, Calif., USA, the disclosure of which is incorporated herein by reference. Kelleher et al. describes electrolyte-assisted tissue ablation of metaplasia in the esophagus by means of a shaft with an expandable barrier that is deployable from the shaft's distal end. An electrode and a temperature/impedance sensor are mounted on the shaft. The shaft may be a catheter formed with several lumens that are used independently for housing optical elements and for transferring fluid.

In the operation of the device, the distal end of the shaft or catheter is placed in the esophagus proximal the cardia. The barrier is then deployed to the cardia and expanded to seal the esophagus from the stomach. The esophageal volume between the barrier and the catheter is partially flooded with a conducting medium and the electrode is deployed into the conducting medium. The sensor is also deployed into contact with the tissue to be ablated. Using open-loop control, or using temperature, impedance, or visual monitoring for closed-loop control, the metaplasia is ablated by passing RF energy from the electrode and through the conducting medium for contact with the tissue being ablated.

Kelleher et al. limits the RF power to a moderate level by using the closed-loop control, wherein the output of the temperature sensors near the electrode is used to control power delivery. However, a disadvantage of Kelleher et al. is that enlargement of the coagulated volume is at the expense of slower coagulation speed and prolonged treatment time.

Another example of electrolyte-assisted ablation is described in U.S. Pat. No. 5,348,554 to Imran et al., assigned to Cardiac Pathways Corporation, Sunnyvale, Calif., USA, the disclosure of which is incorporated herein by reference. Imran et al. includes a catheter constructed of an elongate member having proximal and distal extremities. A metal conducting electrode is secured to the distal extremity of the elongate member and has a chamber formed therein. A conductor extends through the elongate member from the proximal to the distal extremity for supplying RF energy to the electrode. The elongate member has a lumen in the distal extremity, which is in communication with the chamber. A coolant is disposed in the chamber and in contact with the electrode for dissipating heat created in the electrode by the application of RF energy thereto. A disadvantage of Imran et al. is that the coagulated volume is limited due to the relatively small diameter of the electrode used.

Other examples of cooled electrodes include U.S. Pat. No. 5,100,388 to Behl et al., which describes a catheter having a conductive material delivery lumen and a distal tip heating element, suitable for hollow body organs, such as the gall bladder. U.S. Pat. No. 5,304,214 to DeFord et al., describes an RF ablation device specifically designed to selectively ablate prostatic tissue about the prostatic urethra. The disclosures of these patents are incorporated herein by reference. A disadvantage of Behl et al. or DeFord et al. is that the structure of these devices is custom-made to fit a particular anatomy and is not generally suitable for any other anatomy in the body. They also suffer from limited coagulated volume that is possible with the electrode.

In order to overcome the limitation of the small coagulated volume associated with a fine linear needle electrode, U.S. Pat. Nos. 5,431,649 and 6,016,809 to Mulier et al., assigned to Medtronic, Inc., Minneapolis, Minn., USA, the disclosures of which are incorporated herein by reference, propose a hollow helical electrode, with injection of a cooled conducting liquid.

In general, Mulier et al. is directed to treatment of tachyarrhythmias, wherein one or more chambers of the heart exhibit an excessively fast rhythm. In particular, Mulier et al. is directed to treatment of tachycardias, which are due to the presence of ectopic foci within the cardiac tissue or due to the presence of aberrant condition pathways within the cardiac tissue. In Mulier et al., a catheter is provided with a hollow, helical electrode, which is screwed into cardiac tissue at a desired ablation site and connected to a source of RF electrical energy to ablate the tissue adjacent the electrode. Prior to ablation, it is essential to inject a conductive fluid through the hollow needle, which cools the tissue adjacent the needle and increases the conductivity of the tissue in the area of the electrode.

The helical electrode provides an enlarged surface area as compared to relatively straight or needle-like electrodes for insertion into the endocardium, and also serves to stabilize the location of the catheter during the application of the RF signal. In addition, there is essentially no bleeding following removal of the helical electrode, so it can safely be placed in multiple locations for mapping and ablation purposes.

Mulier et al. uses a non-toxic, non-arrhythmogenic, conductive solution such as Ringer's solution to the area of the electrode, before and during application of RF energy. The helical electrode is hollow, and the conductive solution is applied through one or more apertures in the electrode. The conductive solution injected prior to application of the RF signal is believed to displace blood in the vicinity of the electrode. Ringer's solution, for example, has a much higher conductivity than blood (approximately 3–4 times higher) or cardiac muscle (approximately 7 times higher). Overall resistance to the induced electrical current is reduced, which is believed to assist in expanding the size of the lesion, by spreading the effective area of application of the electrical current over a wider area. Application of the conductive solution during the burn helps prevent overheating of the tissue, allowing for a prolonged application of the RF signal, extending beyond the point at which burning or charring would otherwise normally occur.

However, liquid handling and adjusting the electrode length to that of the treated area are shortcomings, especially for a relatively large volume. Moreover, a monopolar helical electrode is limited in its ability to deliver power inside the helix and to control the treated boundary outside the helix. Furthermore, local temperature along a long electrode is generally difficult to control, because local temperature varies according to local variations of tissue impedance and current density.

U.S. Pat. No. 6,132,426 to Kroll, assigned to Daig Corporation, Minnetonka, Minn., USA, describes an RF ablation catheter that incorporates therein a positive temperature coefficient (PTC) temperature sensor. The PTC sensor provides a built-in fail-safe current limiter to avoid over-ablating the target tissue, and to prevent coagulation adherence to the catheter electrode tip and damage to the catheter and patient from overheating. However, disadvantages of Kroll include slower coagulation speed and prolonged treatment time.

Some prior art mentions rotation of the ablating electrode. For example, U.S. Pat. No. 6,010,476 to Saadat, assigned to AngioTrax, Inc., Sunnyvale, Calif., USA, describes a device for creating transmural channels for transmyocardial revascularization. The device includes a cutting head that may ablate or cut tissue with RF energy. The cutting head may be coupled to a drive tube and rotated at high speeds by a motor and gearing. However, the rotation of the cutting head is not used to prevent tissue adhesion, rather rotation is used to facilitate entry of the cutting head into the cardiac tissue and to help form transmural channels. Once the electrode has arrived at the desired location, RF energy is applied to the electrode to ablate tissue. Saadat does not mention ablating while rotating the electrode.

U.S. Pat. No. 6,066,134 to Eggers et al., assigned to ArthroCare Corporation, Sunnyvale, Calif., USA, the disclosure of which is incorporated herein by reference, describes an electrosurgical probe that includes a shaft having an electrode array at its distal end and a connector at its proximal end for coupling the electrode array to a high frequency power supply. The shaft includes a return electrode recessed from its distal end and enclosed within an insulating jacket. The return electrode defines an inner passage electrically connected to both the return electrode and the electrode array for passage of an electrically conducting liquid. By applying high frequency voltage to the electrode array and the return electrode, the electrically conducting liquid generates a current flow path between the return electrode and the electrode array so that target tissue may be cut or ablated.

Eggers et al. mentions manually reciprocating or rotating the probe in a light brushing motion, so as to maintain the supply of electrically conducting fluid in the region between the active electrodes and the tissue. The dynamic movement of the active electrodes over the tissue site is used by Eggers et al. to enable the electrically conducting liquid to cool the tissue surrounding recently ablated areas to minimize damage to this surrounding tissue. Eggers et al does not mention ablating while reciprocating or rotating the electrode. Moreover, the dynamic movement is not used by Eggers et al. to prevent tissue adhesion. Identical use of reciprocation of the probe during electrosurgical tissue revascularization is discussed in U.S. Pat. No. 6,102,046 to Weinstein et al., also assigned to ArthroCare Corporation, the disclosure of which is incorporated herein by reference.

SUMMARY OF THE INVENTION

The present invention seeks to provide novel electrosurgical apparatus for RF tissue ablation that solves the above-mentioned problems of the prior art.

The electrosurgical apparatus of the present invention comprises a manipulator that moves electrodes in a controlled manner while RF power is delivered to the electrodes. Unlike the prior art, the RF electrode may ablate during controlled motion thereof. This motion helps prevent tissue-electrode adhesion. The motion may be unidirectional along the length of the treated volume, or alternatively may comprise reciprocating motion, vibration or combinations of different kinds of motion. The motion of the electrode is preferably along the electrode trajectory, i.e., linear motion for linear electrodes and helical motion for helical electrodes.

The electrode is at the distal tip of an electrically insulated support. The electrode may be monopolar or bipolar, hollow or non-hollow. The electrode may be linear or may be a short segment at the tip of a helical, insulated support. The electrode itself may be helical. For example, the electrode may be configured as a monopolar electrode, with a single or multiple-helix as the active (current emitting) electrode, or as a bipolar electrode with single or multiple helix-pairs. Alternatively, a bipolar electrode may comprise a single or multiple-helix as one electrode and a conducting central rod as the other electrode.

In one embodiment of the present invention, the electrodes are configured as a pair of bipolar concentric (sharing a common center) or eccentric (off-center) helices. A plurality of electrodes may be mounted on the same helical insulated support. A central insulated rod may be added to helical electrodes for motion stabilization. Additional possible electrodes configurations may be obtained by using straight needles instead of helices.

The helical electrode assembly may coagulate a cylindrical envelope of tissue, while at the same time sparing a cylinder of tissue at the center of the helix. For example, the helical arrangement may be used to coagulate prostate tissue around the urethra without causing coagulation of the urethra itself. In other treatment plans, it may be desirable to cause necrosis of the inner cylindrical volume of the helical electrode assembly. In such a case, the helical electrode assembly may coagulate the tissue surrounding the inner cylindrical volume in such a way such that the blood supply to the inner non-coagulated cylindrical tissue is cut off. The non-coagulated cylindrical tissue is then left to die due to the absence of a sufficient blood supply from the coagulated cylindrical envelope, thereby increasing the amount of tissue that undergoes necrosis and shortening treatment time.

The manipulator, controlled by a controller, preferably inserts electrodes into the tissue target site (X-direction) at a predetermined YZ position using linear and/or rotational motion. The manipulator may then impart reciprocating motion to the electrodes by reversing the insertion motion. The velocity of the electrode motion may be controlled in various manners, such as by an impedance measurement in a closed-loop fashion. The manipulator may translate the electrodes to a different YZ position prior to subsequent insertion. The electrode assembly may be disposable, and may be easily replaced and attached to the manipulator.

Treatment planning software, based on user interaction with a display of registered anatomical images obtained prior to the treatment, may generate a treatment plan that includes positioning and power delivery instructions to the controller and manipulator.

Imaging apparatus, mechanically or otherwise coupled to the manipulator, determines electrode position during intracorporeal motion in order to facilitate power delivery according to the treatment plan.

There is thus provided in accordance with a preferred embodiment of the present invention electrosurgical apparatus including an electrode adapted to deliver radio frequency (RF) energy to a tissue, an RF energy source in communication with the electrode, a manipulator in operable connection with the electrode, adapted to move the electrode, and a controller in communication with the RF energy source and the manipulator, adapted to control operation of the manipulator and the electrode in accordance with a mode of operation that includes at least the following steps:

a) delivering RF energy to the electrode from the RF energy source sufficient to cause ablation of a tissue, and b) moving the electrode so as to at least diminish adherence of tissue to the electrode.

In accordance with a preferred embodiment of the present invention the electrode has a longitudinal axis and the manipulator is adapted to move the electrode generally along the longitudinal axis.

Further in accordance with a preferred embodiment of the present invention the manipulator is adapted to move the electrode in a reciprocating movement.

Still further in accordance with a preferred embodiment of the present invention the manipulator is adapted to vibrate the electrode in at least two directions.

Additionally in accordance with a preferred embodiment of the present invention the electrode includes an insulating support, and the electrode and insulating support are configured as an electrode assembly that has a generally helical shape.

In accordance with a preferred embodiment of the present invention the manipulator is adapted to screw the electrode assembly into a tissue, wherein the electrode is adapted to cut a helical path into the tissue. The manipulator is preferably adapted to move the electrode back and forth along the helical path.

Further in accordance with a preferred embodiment of the present invention a plurality of the electrode assemblies are provided. A helical pitch of one of the electrode assemblies may be shifted axially with respect to a helical pitch of another of the electrode assemblies.

Still further in accordance with a preferred embodiment of the present invention the electrode has a generally hollow lumen formed therein.

Additionally in accordance with a preferred embodiment of the present invention a fluid source is in fluid communication with the lumen, wherein the lumen is formed with at least one outlet for passage therethrough of the fluid.

In accordance with a preferred embodiment of the present invention imaging apparatus is in communication with the manipulator and/or the controller, the imaging apparatus being adapted to sense motion of the electrode.

Further in accordance with a preferred embodiment of the present invention a central rod passes through a helix of the electrode. The central rod may be electrically conducting or insulating.

In accordance with a preferred embodiment of the present invention a sensor is placed at a distal portion of the electrode, the sensor being in communication with the controller.

Further in accordance with a preferred embodiment of the present invention one of the electrode assemblies is disposed within an inner volume of another of the electrode assemblies. One of the electrode assemblies may be concentric or eccentric with another of the electrode assemblies.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figure 1:
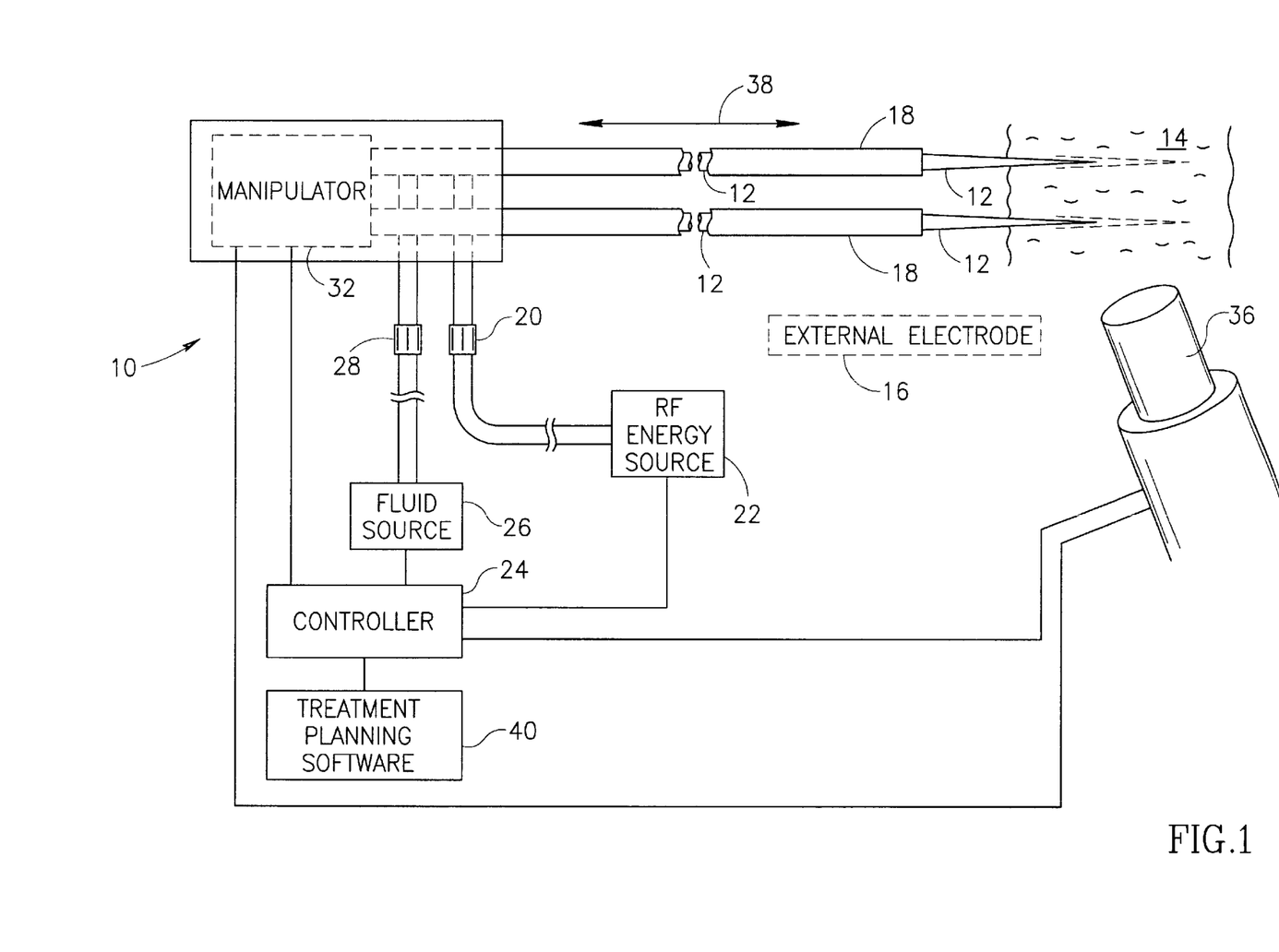
FIG. 1 is a simplified illustration of electrosurgical apparatus constructed and operative in accordance with a preferred embodiment of the present invention, comprising generally straight fine needle electrodes.

Reference is now made to FIG. 1, which illustrates electrosurgical apparatus 10, constructed and operative in accordance with a preferred embodiment of the present invention.

Electrosurgical apparatus 10 preferably includes one or more electrodes 12 adapted to deliver radio frequency (RF) energy to a tissue 14. In FIG. 1, a pair of electrodes 12 are shown, shaped as fine needles and configured to operate as bipolar electrodes. Alternatively, electrode 12 may be used as a monopolar electrode in conjunction with an external electrode 16.

Each electrode 12 is preferably carried by or attached to an insulating support 18. Insulating support 18 may be a non-conducting support, or an insulating coating formed on a support. As another alternative, insulating support 18 may comprise an insulating outer sheath, which may be made of polyurethane, polytetrafluoroethylene (e.g., TEFLON), or any other biocompatible plastic. The electrode 12 is preferably connected at a proximal end thereof to an RF connector 20, which in turn is connected to an RF energy source 22.

Figure 3:
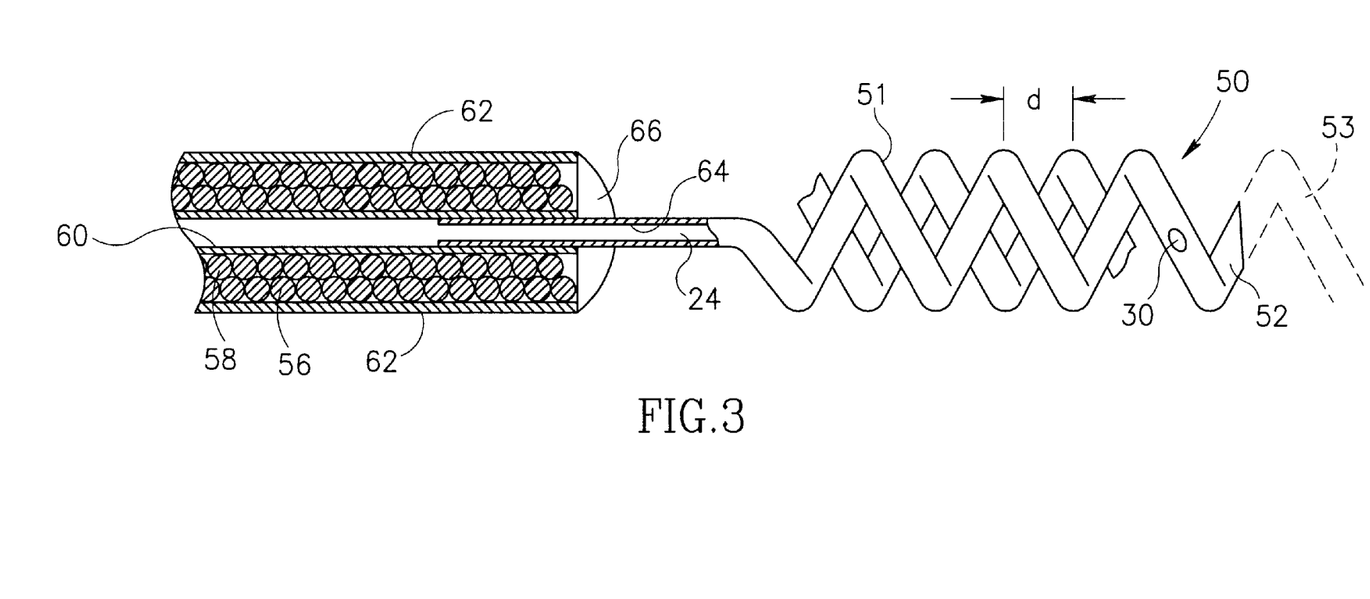
FIG. 3 is a more detailed, partially sectional illustration of the helical electrode assembly of FIG. 2.

In one embodiment of the invention, electrode 12 has a generally hollow lumen 24 formed therein (not seen in FIG. 1, but shown in FIG. 3). A fluid source 26 is in fluid communication with lumen 24, such as by means of a fluid connector 28 (and any suitable valving not shown for the sake of simplicity) positioned at the proximal portion of electrode 12. Lumen 24 is preferably formed with at least one outlet 30 (FIG. 3) for passage therethrough of the fluid. The fluid may be a liquid or gel electrolyte, for example.

A manipulator 32 is in operable connection with each electrode 12. Manipulator 32 may be electrically, pneumatically, hydraulically or mechanically driven, and may include without limitation, a servomotor, step motor, linear actuator, rotary actuator, vibrator or solenoid, for example. Manipulator 32 may be coupled to all electrodes at once so as to move all electrodes generally simultaneously in synchronization with one another. Alternatively, manipulator 32 may be coupled individually to the electrodes so as to be capable of moving the electrodes independently of one another.

A controller 34 is in communication with RF energy source 22 and manipulator 32, and is adapted to control operation of manipulator 32 and electrodes 12 in accordance with a treatment plan or mode of operation, described further hereinbelow.

Imaging apparatus 36 is in communication with controller 34, and may also be in communication with manipulator 32, either by direct coupling therewith or via controller 34. Imaging apparatus 36 determines electrode position during intra-corporeal motion in order to facilitate power delivery according to the treatment plan. For example, imaging apparatus 36 may be a trans-rectal ultrasound probe used for imaging the prostate in conjunction with treatment of benign prostatic hypertrophy (BPH) or a malignant condition. Other examples include fiber optic imaging apparatus, fluoroscopic imaging apparatus, endoscopic imaging apparatus or laparoscopic imaging apparatus, which may be useful in RF tissue ablation to treat gastroesophageal reflux disease (GERD) or as part of transmyocardial revascularization, for example.

In addition to imaging, electrodes 12 may be coupled to other medical sensors or equipment. For example, in RF ablation of cardiac tissue such as in the treatment of tachyarrhythmias, electrodes 12 may be coupled to EKG monitoring equipment (not shown) to assist in determining whether tachycardia persists and whether the tissue in the vicinity of electrodes 12 is still participating in aberrant conduction or ectopic activity, associated with the tachycardia.

It is noted that electrodes 12 may be brought to tissue 14 in any convenient manner, such as by directly piercing into tissue 14 or by delivery by a catheter system (not shown) to the desired site.

In one example of a treatment plan possible with the present invention, manipulator 32, controlled by controller 34, inserts electrodes 12 into the tissue target site generally along a longitudinal axis 38 of the electrodes 12 (referred to as the X axis) at a predetermined YZ (referring to the plane perpendicular to X axis) position using linear and/or rotational motion. RF energy source 22 delivers RF energy to electrodes 12 to perform tissue ablation. Controller 34 may implement treatment planning software 40, based on user interaction with a display of registered anatomical images obtained prior to the treatment, in order to control positioning of and power delivery to electrodes 12.

During RF ablation, manipulator 32 may move electrodes 12 proximally along longitudinal axis 38 (i.e., retracting the electrodes from their inserted position) or may move electrodes 12 in a reciprocating motion generally along longitudinal axis 38. Alternatively or additionally, manipulator 32 may vibrate or oscillate electrodes 12 in at least two directions (along or about the X, Y and Z axes or any combination thereof). (A proximal position of electrodes 12 during reciprocating motion thereof is shown in solid lines in FIG. 1, whereas a distal position of electrodes 12 during reciprocating motion thereof is shown in broken lines in FIG. 1.) The proximal or reciprocating motion or vibration may help prevent tissue adhesion during ablation. The electrodes may then be translated to a different YZ position prior to subsequent insertion into a different tissue site.

Figure 2:
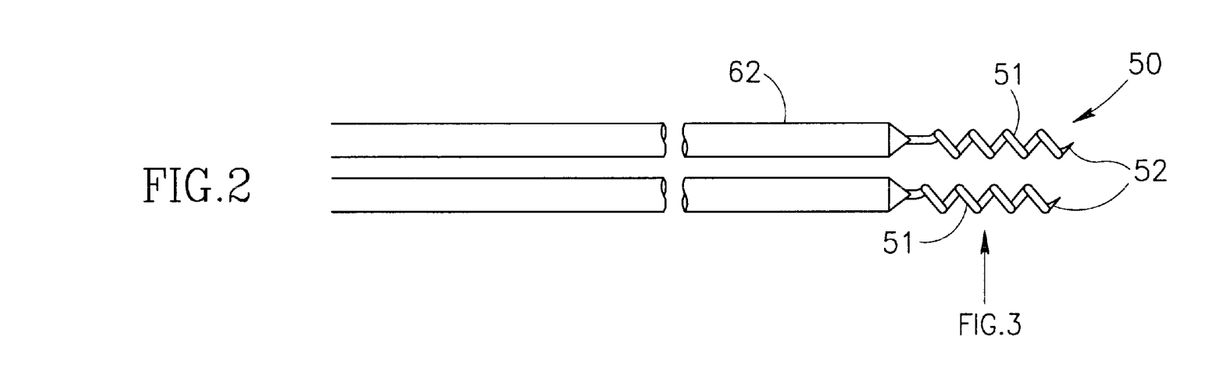
FIG. 2 is a simplified illustration of electrosurgical apparatus constructed and operative in accordance with another preferred embodiment of the present invention, comprising helical electrode assemblies.

Reference is now made to FIGS. 2 and 3, which illustrate electrosurgical apparatus 50 constructed and operative in accordance with another preferred embodiment of the present invention. Electrosurgical apparatus 50 comprises one or more electrodes 52, each of which is preferably carried by or attached to an insulating support 51 that has a generally helical shape. Electrode 52 is preferably a short segment at the tip of the helical support 51. Alternatively, electrode 52 may be helical as well. Insulating support 51 may be constructed of a non-conducting material, coating or sheath as described hereinabove for insulating support 18.

Like electrosurgical apparatus 10, electrosurgical apparatus 50 preferably comprises manipulator 32, RF energy source 22, controller 34 (with treatment planning software 40) and imaging apparatus 36, and may also comprise fluid source 26, all of which are omitted in FIGS. 2 and 3 for the sake of simplicity. The combination of electrode 52 and insulating support 51 is also referred to as an electrode assembly.

Manipulator 32 is adapted to screw each electrode 52 into tissue 14 (FIG. 1), wherein electrodes 52 cut a helical path 53 into tissue 14. One way of transferring torque to the electrode 52 is by means of a torque cable 54, shown in FIG. 3. Torque cable 54 may include two coils 56 and 58, which are wound in opposite directions about a tube 60 housed in an insulating catheter sleeve 62. Such a torque cable is commercially available from Lake Region Manufacturing Company of Chaska, Minn., USA, and is described in U.S. Pat. No. 5,165,421, the disclosure of which is incorporated herein by reference. A proximal portion 64 of the electrode assembly is tightly fit into tube 60 through an end cap 66 of sleeve 62. Coils 56 and 58 may be constructed of metal and serve as conductors.

As mentioned hereinabove, the devices of U.S. Pat. Nos. 5,431,649 and 6,016,809 to Mulier et al., do not move the electrodes during ablation, but rather rely upon the application of a conductive solution to the ablated area to prevent over-ablation. In contrast, in the present invention, manipulator 32 may move electrodes 52 back and/or forth along helical path 53 during ablation. This motion tends to prevent tissue adherence to the electrodes 52. (Of course the present invention may also be carried out by moving the electrode assemblies back and/or forth along helical path 53 even not during ablation.)

In one embodiment of the invention, a helical pitch of one of the electrode assemblies is shifted axially, such as by a distance d (FIG. 3), with respect to the helical pitch of another of the electrode assemblies. The distance d may one one-half pitch, for example. Electrode assemblies with uniform or different pitches may be used.

Figure 4:
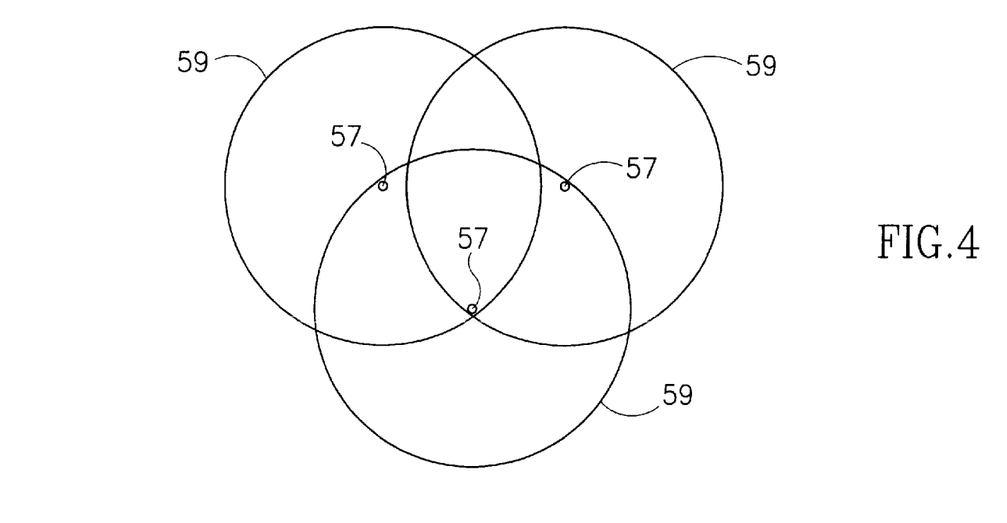
FIG. 4 is a simplified illustration of insertion points and helical path limits cut by the helical electrode assemblies of FIG. 2.

Reference is now made to FIG. 4, which illustrates insertion points 57 and helical path limits 59 cut by electrode 52. The use of axially shifted helices may increase the ablated area around the electrodes 52. As seen in FIG. 4, a plurality of helical electrode assemblies may ablate a relatively large volume of tissue in a plurality of regions, not possible heretofore with the prior art. The electrode assemblies may be configured as monopolar electrodes, with a single or multiple-helix as the active electrode, or as bipolar electrodes with single or multiple helix-pairs.

Figure 5:
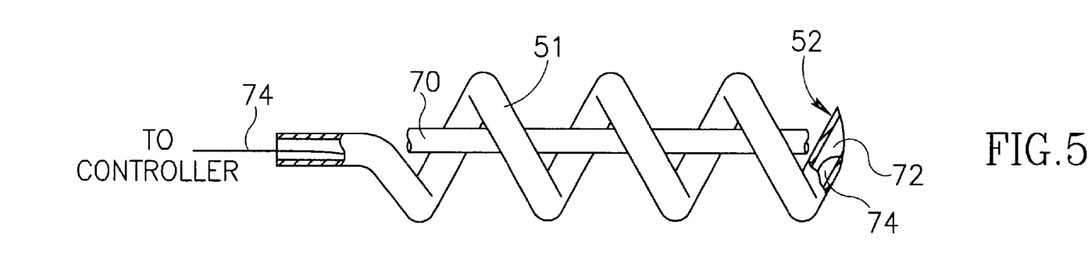
FIG. 5 is a simplified illustration of a helical electrode assembly with a central rod passing therethrough, constructed and operative in accordance with a preferred embodiment of the present invention.

Reference is now made to FIG. 5, which illustrates a central rod 70 passed through the helix of electrode 52. Central rod 70 may be electrically conducting, in which case electrode 52 may be bipolar, wherein electrode 52 is the current emitting electrode and the conducting central rod 70 serves as the other electrode. Alternatively, central rod 70 may be insulated. In such an embodiment, rod 70 may be added to electrodes 52 for motion stabilization.

As seen in FIG. 5, a sensor 72 may be placed at a distal portion of electrode 52 (or electrode 12 of FIG. 1). Sensor 72, which may be in communication with controller 34 via a wire 74 running through electrode 52, may be used in a closed-loop control of apparatus 50 (or 10), by feeding back information to controller 34. For example, sensor 72 may be a temperature sensor, such as a thermocouple or thermistor, and controller 34 controls RF energy levels or movement of the electrode in accordance with the sensed temperature so as to avoid over-ablation or tissue adherence. As another example, sensor 72 may be a capacitance or resistance sensor, which may sense the electrical capacitance or resistance between the electrode and the tissue being ablated. Controller 34 may control RF energy levels or movement of the electrode in accordance with the sensed electrical parameters so as to avoid over-ablation or tissue adherence. For example, the velocity of the electrode motion may be controlled in a closed-loop fashion with an impedance measurement made by sensor 72.

Figure 6A:
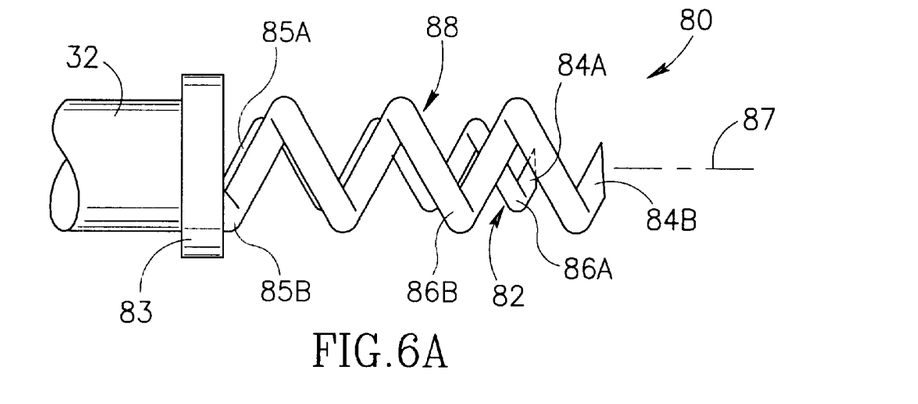
FIGS. 6A and 6B are simplified side-view and end-view illustrations, respectively, of electrosurgical apparatus constructed and operative in accordance with yet another preferred embodiment of the present invention, comprising electrodes configured as a pair of bipolar concentric helices.
Figure 6B:
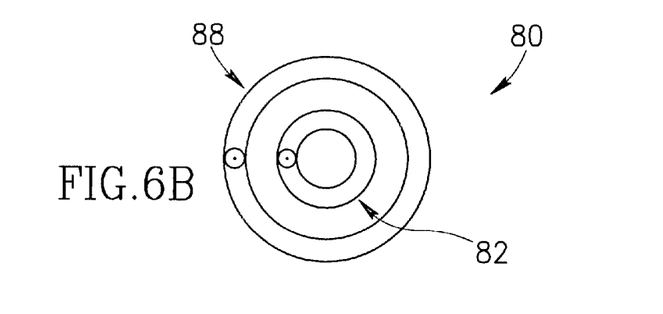

Reference is now made to FIGS. 6A and 6B, which illustrate electrosurgical apparatus 80 constructed and operative in accordance with yet another preferred embodiment of the present invention. Electrosurgical apparatus 80 differs from electrosurgical apparatus 50 in that the electrode assemblies (comprising the electrodes and the insulating supports) are configured as a pair of bipolar concentric helices.

Specifically, referring to FIG. 6A, electrosurgical apparatus 80 comprises an inner electrode assembly 82 that includes an electrode 84A carried by or attached to an insulating helical support 86A, and an outer electrode assembly 88 that includes an electrode 84B carried by or attached to an insulating helical support 86B. Like electrosurgical apparatus 10 and 50, electrosurgical apparatus 80 preferably comprises manipulator 32, RF energy source 22, controller 34 (with treatment planning software 40) and imaging apparatus 36, and may also comprise fluid source 26, all of which (except manipulator 32) are omitted in FIGS. 6A and 6B for the sake of simplicity.

Inner electrode assembly 82 is generally concentric with outer electrode assembly 88, meaning that the two assemblies generally share a common center lying on a longitudinal axis 87. The concentric arrangement, like an individual electrode, is rotatable like a corkscrew. Proximal ends 85A and 85B of both the inner 82 and outer 88 electrode assemblies, respectively, may be attached to a small plate or disc 83. Plate 83 is preferably generally perpendicular to longitudinal axis 87, and is attachable to manipulator 32 for rotating the electrode assemblies 82 and 86.

Figure 7:
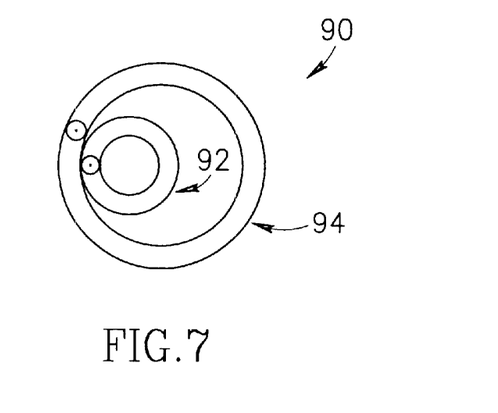
FIG. 7 is a simplified end-view illustration of electrosurgical apparatus constructed and operative in accordance with still another preferred embodiment of the present invention, comprising electrodes configured as a pair of bipolar eccentric helices.

Reference is now made to FIG. 7, which illustrates electrosurgical apparatus 90 constructed and operative in accordance with still another preferred embodiment of the present invention. Electrosurgical apparatus 90 differs from electrosurgical apparatus 80 in that the electrode assemblies (comprising the electrodes and the insulating supports) are configured as a pair of bipolar eccentric helices.

Specifically, referring to FIG. 7, electrosurgical apparatus 90 comprises an inner electrode assembly 92 disposed in an inner volume of an outer electrode assembly 94. The rest of the construction of electrosurgical apparatus 90 and its operation is preferably similar to that described for electrosurgical apparatus 80. It is appreciated that other arrangements of helical pairs of electrode assemblies are also within the scope of the invention.

Figure 8A:
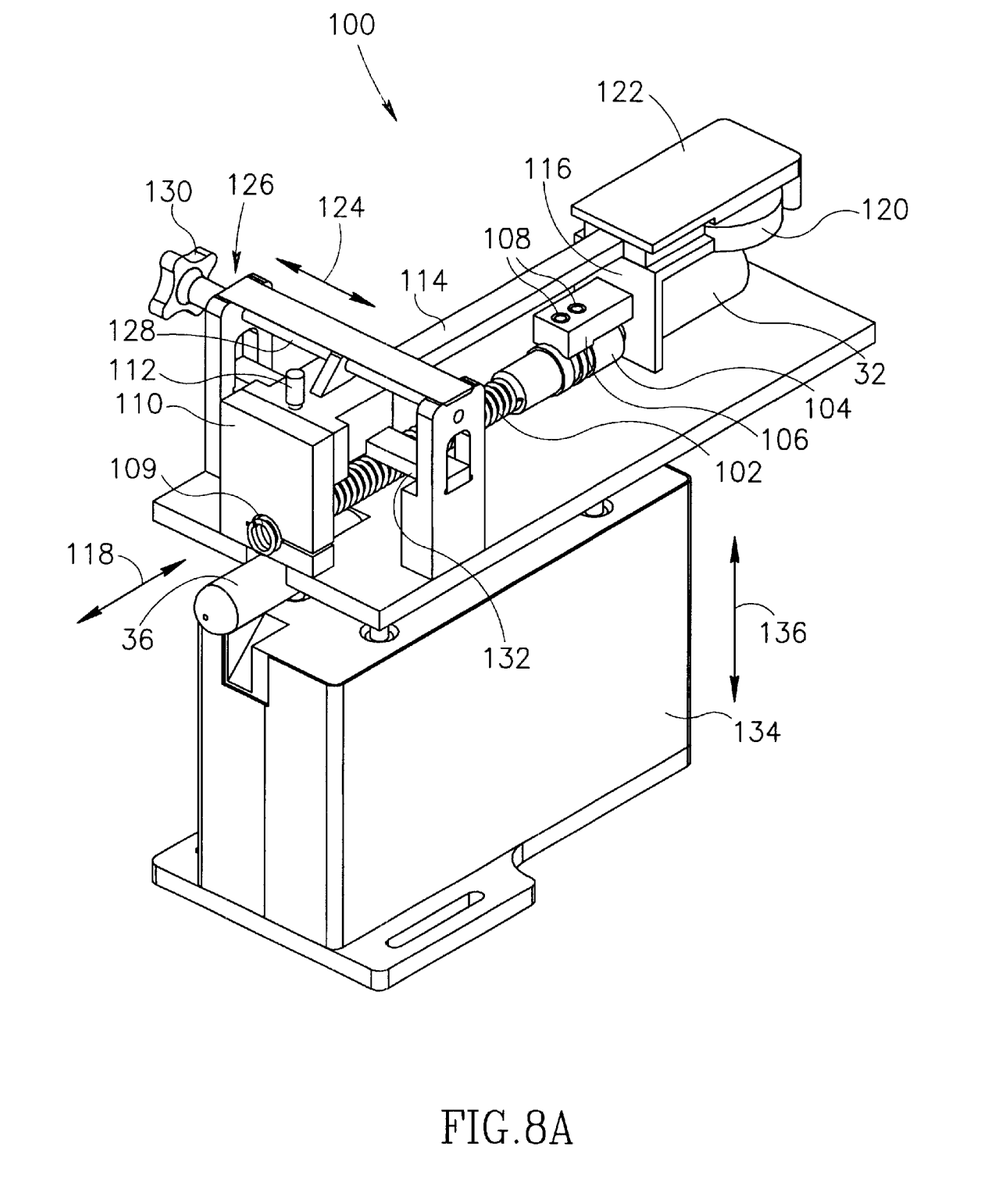
FIGS. 8A, 8B and 8C are simplified pictorial, side-view and end-view illustrations, respectively, of electrosurgical apparatus constructed and operative in accordance with still another preferred embodiment of the present invention, comprising electrodes configured as a pair of bipolar helices.
Figure 8B:
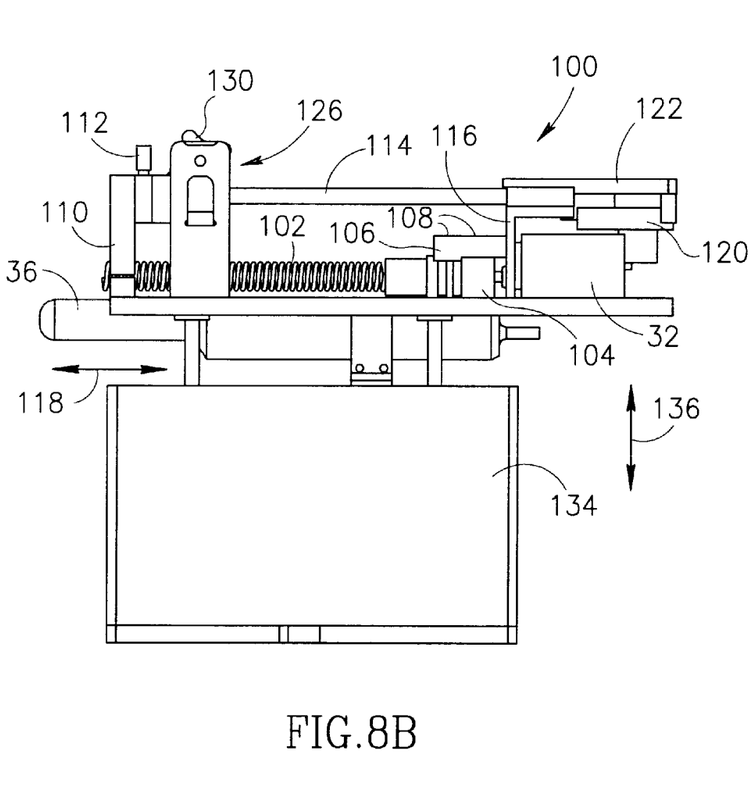
Figure 8C:
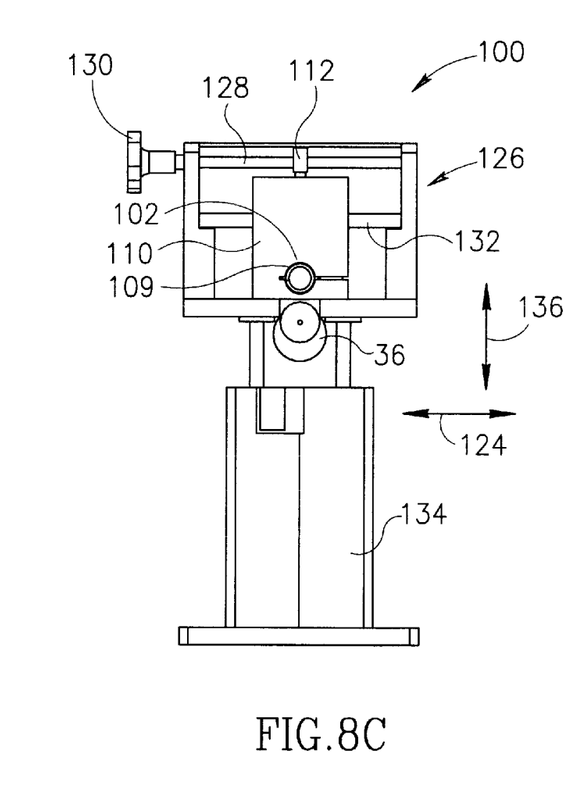

Reference is now made to FIGS. 8A, 8B and 8C, which illustrate electrosurgical apparatus 100 constructed and operative in accordance with still another preferred embodiment of the present invention. Electrosurgical apparatus 100 employs a helical electrode assembly 102, constructed like any of the helical electrode assemblies described hereinabove (monopolar, bipolar, concentric, eccentric and the like).

A proximal end of helical electrode assembly 102 is preferably coupled by means of a coupling 104 to manipulator 32 for rotating the electrode assemblies and screwing them into and out of a tissue (not shown). The electrode assemblies 102 may be energized with RF energy from RF energy source 22 (not shown in FIGS. 8A–8C) via slip rings 106. Slip rings 106 may have a pair of stationary terminals 108 for connection to RF energy source 22.

A distal end of helical electrode assembly 102 is preferably guided through an aperture 109 of a nut plate 110. Nut plate 110 is preferably secured, such as by means of a pin 112, to a longitudinal guide rail 114. Manipulator 32 may be also secured to guide rail 114 by means of a bracket 116 that has a U-shaped channel that receives guide rail 114. As manipulator 32 advances or retracts the helical electrode assembly 102 along a longitudinal axis 118 of the assembly 102, the manipulator 32 travels together with assembly 102. The movement of assembly 102 along longitudinal axis 118 may be measured by a linear displacement measuring device 120, such as a potentiometer or linear encoder. Linear displacement measuring device 120 may be provided with a cover 122.

The helical electrode assembly 102 may be moved or adjusted along a transverse axis 124, generally perpendicular to longitudinal axis 118. This may be accomplished by attaching the electrode assembly 102 to a transverse adjustment assembly 126, which may comprise a threaded rod 128 to which assembly 102 is attached. Rod 128 may be turned by means of a handle 130 to adjust the position of assembly 102 along axis 124. Assembly 102 may slide along a bar 132 during the transverse movement.

Electrosurgical apparatus 100 and imaging apparatus 36 (which may be an ultrasound probe) are preferably mounted on a translator assembly 134. Translator assembly 134 is adapted to move electrosurgical apparatus 100 and imaging apparatus 36 generally along axis 118 or another axis 136, generally perpendicular to longitudinal axis 118.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. Electrosurgical apparatus comprising:

a plurality of helical shaped electrode assemblies adapted to deliver radio frequency (RF) energy to a tissue; and a manipulator in operable connection with said electrode assemblies, operative to move said electrode assemblies, wherein one of said electrode assemblies has a smaller diameter than another of said electrode assemblies and is disposed within an inner volume of said other electrode assembly.

2. Electrosurgical apparatus according to claim 1 wherein the smaller diameter electrode assembly is concentric with said other electrode assembly.

3. Electrosurgical apparatus according to claim 1 wherein the smaller diameter electrode assembly is eccentric with said other electrode assembly.

* * * * *